(12) United States Patent
Viola

(10) Patent No.: US 9,173,714 B2
(45) Date of Patent: Nov. 3, 2015

(54) MAGNETICALLY SECURED SURGICAL STATION WITH FORCE MODULATION

(75) Inventor: Frank J. Viola, Sandy Hook, CT (US)

(73) Assignee: Covidien LP, Mansfield, MA (US)

(*) Notice: Subject to any disclaimer, the term of this patent is extended or adjusted under 35 U.S.C. 154(b) by 491 days.

(21) Appl. No.: 13/038,504

(22) Filed: Mar. 2, 2011

(65) Prior Publication Data

US 2011/0230726 A1 Sep. 22, 2011

Related U.S. Application Data

(60) Provisional application No. 61/315,215, filed on Mar. 18, 2010.

(51) Int. Cl.
*A61B 1/32* (2006.01)
*A61B 19/00* (2006.01)
*A61B 17/00* (2006.01)

(52) U.S. Cl.
CPC ................ *A61B 19/26* (2013.01); *A61B 19/22* (2013.01); *A61B 2017/00283* (2013.01); *A61B 2017/00411* (2013.01); *A61B 2017/00876* (2013.01); *A61B 2019/2253* (2013.01); *A61B 2019/2265* (2013.01)

(58) Field of Classification Search
CPC ............. A61B 19/22; A61B 17/00234; A61B 2017/00283; A61B 2017/00411; A61B 2017/00876

USPC .............. 606/54–59, 130; 600/9, 12, 15, 600/231–233, 201; 5/601, 621, 624; 602/32–40; 128/845; 378/209
See application file for complete search history.

(56) References Cited

U.S. PATENT DOCUMENTS

| | | | |
|---|---|---|---|
| 6,358,196 B1* | 3/2002 | Rayman | 600/12 |
| 7,850,591 B2* | 12/2010 | Spector | 600/12 |
| 2004/0050395 A1 | 3/2004 | Ueda et al. | |
| 2006/0074448 A1* | 4/2006 | Harrison et al. | 606/237 |
| 2006/0149135 A1* | 7/2006 | Paz | 600/201 |
| 2007/0073102 A1 | 3/2007 | Matsuno et al. | |
| 2007/0135685 A1 | 6/2007 | Cuschieri | |
| 2008/0004634 A1 | 1/2008 | Farritor et al. | |
| 2008/0058835 A1 | 3/2008 | Farritor et al. | |

* cited by examiner

*Primary Examiner* — Anu Ramana
*Assistant Examiner* — Jessica Weiss

(57) ABSTRACT

An anchoring device for use within a body cavity during a surgical procedure is disclosed. The anchoring device includes an external assembly, an internal assembly, a controller, and a module. The external assembly has a first magnetic component. The internal assembly has a second magnetic component. The internal assembly is sized to be placed inside of the body cavity. The electrical current is connected with one of the first and the second magnetic component to produce a magnetic field about the connected magnetic component to approximate the internal and external assemblies. The module determines a parameter and is in communication with a controller. The controller controls the electrical current in response to the parameter.

7 Claims, 4 Drawing Sheets

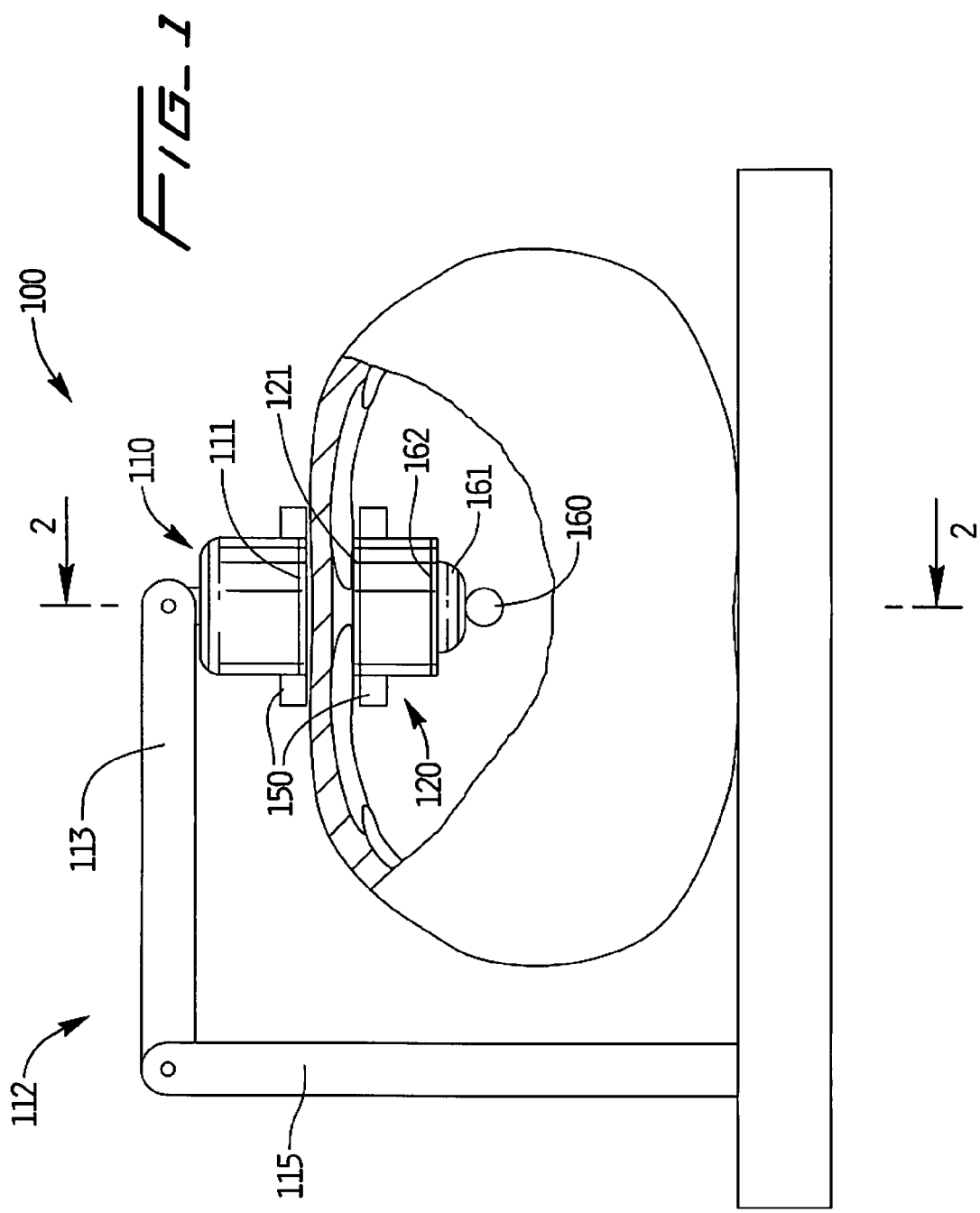

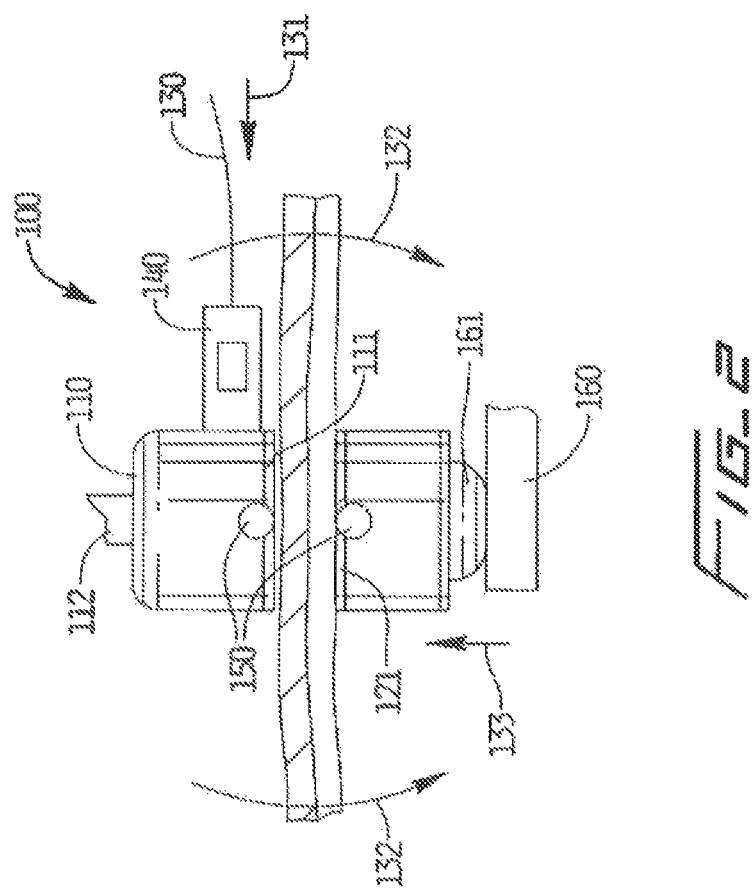

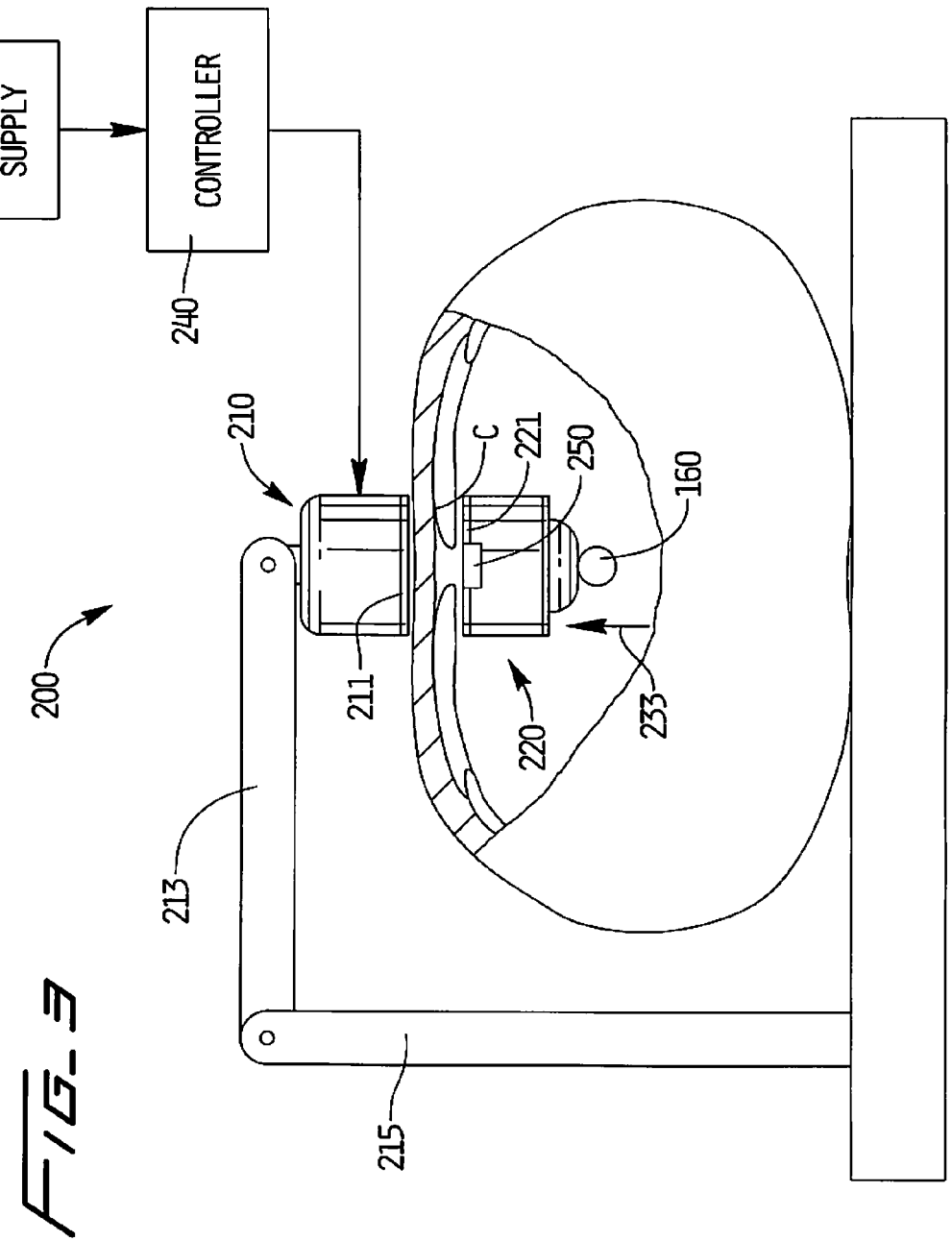

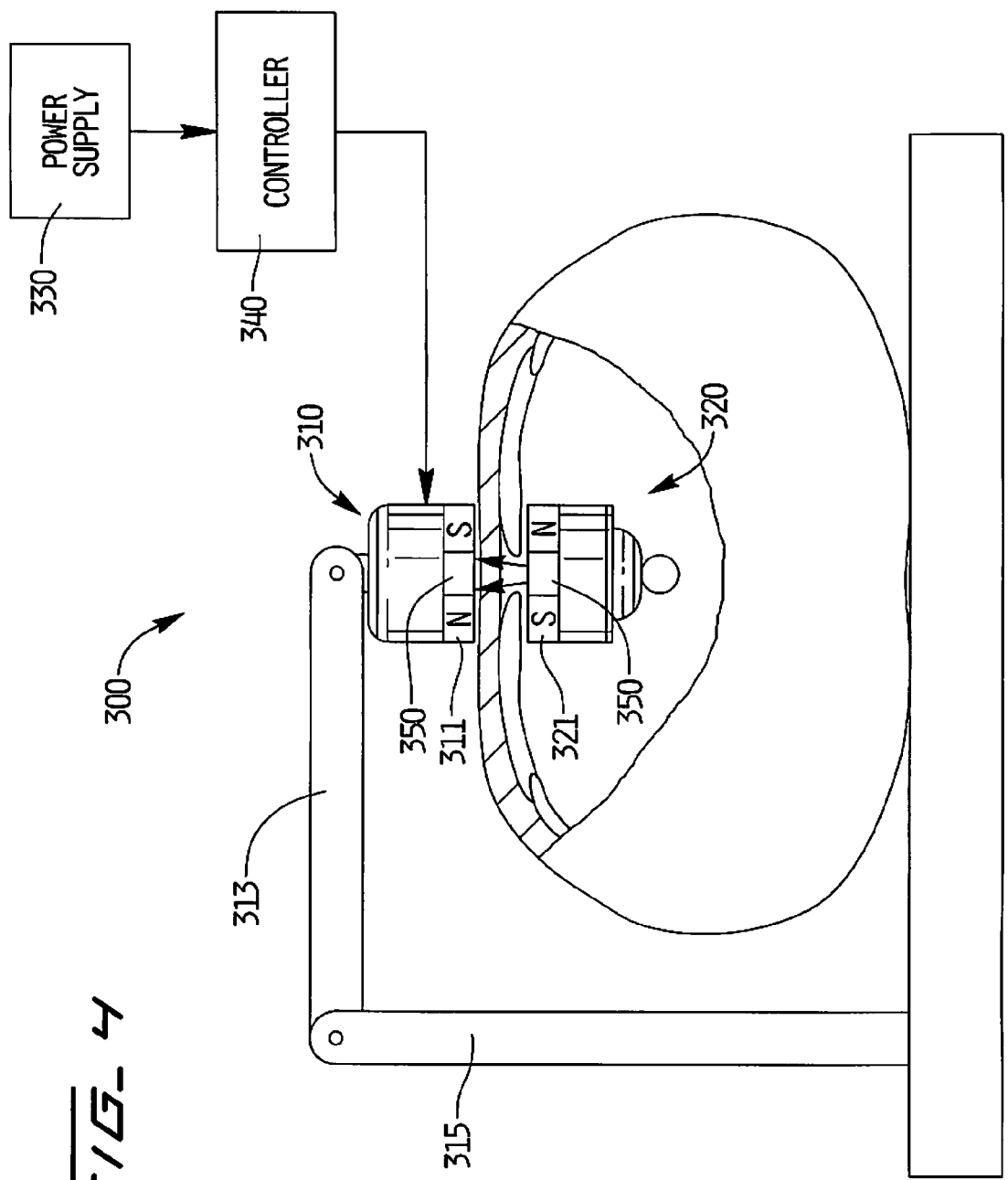

MAGNETICALLY SECURED SURGICAL STATION WITH FORCE MODULATION

This application claims priority from provisional application Ser. No. 61/315,215, filed Mar. 18, 2010, the entire contents of which are incorporated herein by reference.

BACKGROUND

1. Technical Field

The present disclosure relates to a device for use in a minimally invasive surgery and more particularly, to an anchoring device which is retained and movably arrangeable inside of a body cavity.

2. Related Art

Laparoscopy is minimally invasive surgery (MIS) performed in the abdominal cavity. It has become the treatment of choice for several routinely performed interventions.

However, known laparoscopy technologies are limited in scope and complexity due in part to 1) mobility restrictions resulting from using tools inserted through access ports, and 2) limited visual feedback. That is, long laparoscopic tools inserted through small incisions in the abdomen wall limit the surgeon's range of motion and therefore the complexity of the surgical procedures being performed. Similarly, using a 2-D image from a typical laparoscope inserted through a small incision limits the overall understanding of the surgical environment. Further, current technology requires a third port to accommodate a laparoscope (camera), and each new port requires an additional incision.

There is a need in the art for improved surgical methods, systems, and devices for minimally invasive surgery.

SUMMARY

The present disclosure pertains to an anchoring device for use within a body cavity during a surgical procedure. In one aspect, the anchoring device includes an external assembly, an internal assembly, a controller, and a distance sensing module. The external assembly has a first magnetic component. The internal assembly has a second magnetic component and is sized to be placed inside the body cavity through a cannula or surgical access port. The controller is provided for controlling an electrical current and is connected with one of the first and second magnetic components to produce a magnetic field about the connected component. The magnetic field provides a coupling force to approximate the internal assembly and the external assembly. The distance sensing module determines a distance between the external assembly and the internal assembly and is in communication with the controller. The controller controls the electrical source in response to the distance determined by the distance sensing module.

In some embodiments either the first or the second magnetic component can include an electromagnet and the other can include a ferromagnetic material.

The internal assembly may support one or more surgical instruments which can be removably attached thereto. Examples of surgical instruments include, but are not limited to, a camera, an illumination source, a grasper, a retractor, and a device with a sensor. The internal assembly may include a pod having an attachment structure that is complementary to a portion of the internal assembly. The pod may include a surgical instrument.

An external support frame may be connected to the external assembly, and the external assembly may be movably attached to the support frame.

It is envisioned that an electrical source can in some embodiments be connected with both the first magnetic component and second magnetic component.

According to another aspect of the present disclosure, an anchoring device for use within a body cavity during a surgical procedure is disclosed which includes an external assembly, an internal assembly, an electrical source, a controller, and a module. The external assembly has a first magnetic component. The internal assembly has a second magnetic component and is sized to be placed inside the body cavity through a cannula or surgical access port. The controller is provided for controlling an electrical current and is electronically connected with one of the first and second magnetic components to produce a magnetic field about the connected component. The magnetic field provides a coupling force to approximate the internal assembly and the external assembly. The coupling force provides a force from the internal assembly against a wall of the body cavity.

In one embodiment, a module comprising a force sensing module is provided that determines a magnitude of the coupling or attraction force. The force module is in communication with the controller. The controller is connected to the electrical source to control the electrical current in response to the magnitude determined by the force module.

In another embodiment, a module comprising a density module is provided that determines a density of the wall between the external assembly and the internal assembly. The density module is in communication with the controller. The controller is connected to the electrical source to control the electrical current in response to the distance determined by the module.

BRIEF DESCRIPTION OF THE DRAWINGS

The accompanying drawings, which are incorporated in and form part of the specification, illustrate the present disclosure when viewed with reference to the description, wherein:

FIG. 1 is a partial cutaway view of an anchoring system in accordance with a first embodiment of the present disclosure, illustrating an external frame structure and an internal platform;

FIG. 2 is a side cross-sectional view of the anchoring system of FIG. 1 taken along section line 2-2 of FIG. 1;

FIG. 3 is a partial cutaway view of an anchoring system in accordance with another embodiment of the present disclosure, illustrating an external frame structure and an internal platform; and FIG. 4 is a partial cutaway view of an anchoring system in accordance with still another embodiment of the present disclosure, illustrating an external frame structure and an internal platform.

Other features of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed anchoring device for use within a body cavity during a surgical procedure are described in detail with reference to the drawings, in which like reference numerals designate identical or corresponding elements in each of the several views. As used herein, the term "distal" refers to that portion of the surgical device, or component thereof, further from the user while the term "proximal" refers to that portion of the surgical device or component thereof, closer to the user.

Turning now to FIGS. 1 and 2, anchoring (or suspension) system 100 generally includes an external assembly 110, an internal assembly 120, an electrical source 130, a controller 140, and a distance sensing module 150. The internal assembly 120 provides a stationary internal platform or base for supporting surgical instruments inside the body cavity. The external assembly 110 provides a non-invasive system to support and retain the internal assembly 120 in place during the procedure. This is achieved by the magnetic force described below.

The external assembly 110 has a first magnetic component 111. The internal assembly 120 has a second magnetic component 121 and is sized to be placed inside the body cavity through a cannula or surgical access port or directly through an incision. Magnetic component as used herein includes a component composed of a material capable of producing a magnetic field or any material that reacts to or is affected by a magnetic field. Typically, the cannula or port is sized to be between 10 and 12 mm, although other dimensions are contemplated.

The electrical source 130 includes an electrical current 131 connected with either the first or the second magnetic component 111, 121 to produce a magnetic field 132 about the connected component. (In FIG. 2, it is shown connected to first magnetic component 111). The electrical source may be a battery. The magnetic field 132 provides a coupling force 133 in a direction to approximate the internal assembly 120 and the external assembly 110 about a wall of the body cavity. Such force secures (couples) the internal assembly 120 in position with respect to the external assembly 110 and can cause the internal assembly 120 to abut an internal wall of the body cavity.

The coupling attraction force 133 is dependent on the magnetic field 132 and a distance between the first and second magnetic components 111, 121. The distance has an inverse relationship on the coupling force 133 as the attraction force between a magnet and magnetic material varies as the inverse of the square of the distance between them. Thus, as the distance between the components 111, 121 shortens and the magnetic field 132 is held constant, the coupling force 133 increases.

It is understood that applying clamping forces on the abdominal wall drives fluid from the tissue. Thus, the coupling of the first and second magnetic components 111, 121 about the wall forces or squeezes body fluid from between the coupled components 111, 121. As a result, if not adjusted, the clamping pressure or coupling force 133 will increase in magnitude against the wall of the body cavity between external and internal assemblies 110, 120 due to the thinning of tissue or a decrease in the thickness of the wall as body fluids that were in the wall at the beginning of the procedure are forced out from between the assemblies 110, 120 during the procedure. If allowed to continue, tissue trauma could occur.

The system of the present disclosure is designed to adjust the clamping force in accordance with the thickness of the abdominal wall to avoid excessive clamping.

In one embodiment, this is achieved by the distance sensing module 150 which determines the distance between the external assembly 110 and the internal assembly 120. The distance may be determined in a variety of ways that are currently known in the art. One way to determine distance, though not meant to be limiting, includes an ultrasound generator and a receiver.

The distance module 150 sends a constant signal to the controller 140. The signal is proportional or related to the distance between assemblies 110, 120. The controller 140 is connected to the electrical source 130. As the distance decreases, the controller 140 modulates the current to lower the electrical current 131. As a result, the magnetic field 132 is decreased to decrease the clamping force of the assemblies 110, 120. Conversely, should the distance increase, such as if a heavy weight or force is applied to assembly 120 such as by manipulation or supporting organs, the controller 140 modulates the current to increase the electrical current 131. As a result, the magnetic field 132 is increased to increase the clamping force.

In one embodiment, either the first or the second magnetic component 111, 121 is an electromagnet and the other includes a ferromagnetic material.

The internal assembly 120 (as well as internal assemblies 220, 230 described below) supports one or more surgical instruments 160. Examples of surgical instruments include, but are not limited to, a camera, an illumination source, a grasper, a retractor, and a device with a sensor.

The internal assembly may include a pod 161. The pod 161 has an attachment structure 162 that is complementary to a portion of the internal assembly 120. The pod may include the surgical instrument 160. The surgical instrument 160 can be inserted with the internal assembly 120 or alternatively inserted through another access port and connected to the internal assembly 120 within the body cavity. The surgical instrument 160 is shown schematically in the drawings.

The external assembly 110 may be connected to an external support frame 112. More particularly, the support frame 112 may include an arm 113 pivotally attached to support 115. The arm 113 would allow movement of the external assembly 110, which in turn moves (repositions) the internal assembly 120 due to the coupling force. Consequently, the instruments attached to the internal assembly 120 can be moved as a unit inside the body cavity by moving the external assembly 110. Arm 113 can be attached to support 115 for movement in various planes, e.g. toward and away from the patient's body, and across the patient's body.

Each of the magnetic components includes a polarity. It is envisioned that the magnetic components, or at least a portion thereof, have a different polarity.

It is also envisioned that the anchoring device 100 could contain multiple distance modules 150. The use of multiple distance modules 150 can be used to calibrate and verify the distance measurements.

A second embodiment of a surgical anchoring system 200 is illustrated in FIG. 3. The system 200 measures a different parameter than surgical system 100 to adjust the clamping force of the internal and external assemblies.

Surgical system 200 is substantially similar to surgical system 100 and will only be described as relates to the differences therebetween. The anchoring system 200 includes an external assembly 210 mounted to arm 213 extending from support frame 215, an internal assembly 220, and an electrical source 230 and controller 240 similar to electrical source 130 and controller 140 of the embodiment of FIGS. 1 and 2. The system also includes a force sensing module 250. The electrical source can be connected to a first magnetic component 211 on the external assembly 210 or connected to a second magnetic component 221 on the internal assembly 220.

The coupling (or attraction/clamping) force 233 causes the internal assembly 220 to abut against a wall of the body cavity C. (Note the body cavity is shown schematically). The force module 250 determines a magnitude of the coupling force 233. The coupling force may be determined in a variety of ways that are currently known in the art. One way to determine force, though not meant to be limiting, includes a strain gauge to measure a deflection of a cantilever (not shown for clarity). Another way to measure the force 233 is by using a simple pressure switch.

The force sensing module 250 sends a signal to the controller 240. The signal is determined by the coupling force 233. As the force 233 increases, the controller 240, connected to the electrical source 230, modulates the current to lower the electrical current. As a result, the magnetic field is decreased and thus the clamping force applied by the internal assembly 220 and external assembly 210 is reduced. Conversely, should the force 233 decrease in magnitude, the controller 240 modulates the current to decrease the electrical current. As a result, the magnetic field is increased.

A third embodiment of a surgical system 300 is illustrated in FIG. 4 which measures yet another parameter for adjusting the clamping force. In this embodiment, a parameter of the abdominal wall is measured. Surgical system 300 is substantially similar to surgical system 100 and will only be described as relates to the differences therebetween. In the embodiment shown in FIG. 4, the anchoring device includes an external assembly 310 mounted to arm 313 extending from support 315, an internal assembly 320, and an electrical source 330 and a controller 340 similar to electrical source 130 and controller 140 of FIGS. 1 and 2. The system 300 also includes a density module 350. The electrical source can be electrically connected to a first magnetic component 311 on the external assembly 310 or a second magnetic component 321 on the internal assembly 320.

The density sensing module 350 determines a density of the abdominal wall. The density of the wall may be determined in a variety of ways that are currently known in the art. One way to determine density, though not meant to be limiting, includes comparing a signal received with the known signal that was sent.

The density module 350 sends a signal to the controller. The signal is determined by the density of the wall. As the density decreases, the controller 340, connected to the electrical source, modulates the current to lower electrical current. As a result, the magnetic field is decreased to decrease the clamping (or attraction/coupling) force of the internal and external assemblies 320, 310. Conversely, should the density increase in magnitude, the controller 340 modulates the current to increase the electrical current. As a result, the magnetic field is increased to increase the clamping force.

It is also contemplated that parameters other than those described above can be measured and utilized for adjusting the clamping force of the internal assembly and external assembly.

Note the dual polarity of FIG. 4 on the internal and external assemblies could also be utilized with the internal and external assemblies of the embodiments of FIGS. 1 and 2. Similarly, the magnets (polarity) of the FIG. 1 embodiment can be used with the embodiment of FIG. 4.

From the foregoing and with reference to the various drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An anchoring device for use within a body cavity during a surgical procedure, the anchoring device comprising:
   an external assembly having a first magnetic component;
   an internal assembly having a second magnetic component, the internal assembly being sized for placement inside the body cavity;
   an electrical source supplying an electrical current, the electrical source being connected with one of the first magnetic component and the second magnetic component, the electrical current producing a magnetic field about the connected magnetic component, the magnetic field providing an attraction force to draw together the internal assembly and the external assembly, the attraction force providing a reaction force from a wall of the body cavity against the internal assembly
   a controller operably connected to the electrical source; and
   a force module disposed within the internal assembly, the force module configured to determine a magnitude of the reaction force, the force module being in operable communication with the controller, the controller providing an electrical resistance to control the electrical current in response to the magnitude determined by the force module.

2. An anchoring device of claim 1, wherein the internal assembly includes a surgical instrument removably attached thereto.

3. An anchoring device of claim 1, further comprising a pod, the pod having an attachment structure that is complementary to a portion of the internal assembly.

4. An anchoring device of claim 3, wherein the pod includes a surgical instrument selected from the group comprising a camera, an illumination source, a grasper, a retractor, and a sensor.

5. An anchoring device of claim 1, further comprising an external support frame connected to the external assembly and configured to move the external assembly.

6. An anchoring device of claim 1, wherein the electrical source is connected with both the first magnetic component and second magnetic component.

7. An anchoring device for use within a body cavity during a surgical procedure, the anchoring device comprising:
   an external assembly having a first magnetic component;
   an internal assembly having a second magnetic component, the internal assembly being sized for placement inside the body cavity;
   an electrical source supplying an electrical current, the electrical source being connect with one of the first magnetic component and the second magnetic component, the electrical current producing a magnetic field about the connected magnetic component, the magnetic field providing an attraction force controlled by a force module, the attraction force creating a reaction force from a wall of the body cavity against the internal assembly; and
   a controller operably connected to the electrical source;
   wherein the force module is disposed within the internal assembly, the force module configured to determine a magnitude of the reaction force, the force module being in operable communication with the controller, the controller providing an electrical resistance to control the electrical current in response to the magnitude determined by the force module.

* * * * *